United States Patent [19]

Conley et al.

[11] Patent Number: 4,457,673
[45] Date of Patent: Jul. 3, 1984

[54] PUMP AND ACTUATOR MECHANISM

[75] Inventors: Michael G. Conley, El Cerrito; James S. Petrek, Berkeley, both of Calif.

[73] Assignee: Novacor Medical Corporation, Oakland, Calif.

[21] Appl. No.: 446,453

[22] Filed: Dec. 3, 1982

Related U.S. Application Data

[63] Continuation-in-part of Ser. No. 211,210, Nov. 28, 1980, Pat. No. 4,384,829.

[51] Int. Cl.$^3$ .............................................. F04B 43/04
[52] U.S. Cl. ........................................ 417/412; 3/1.7; 92/50; 128/1 D; 128/DIG. 3; 310/22; 310/33
[58] Field of Search ................... 417/410-413, 417/415-417, 472, 478; 128/1 D, DIG. 3; 3/1.7; 310/21, 22, 25, 28, 32, 33; 92/50, 90

[56] References Cited

U.S. PATENT DOCUMENTS

| | | |
|---|---|---|
| 1,893,776 | 1/1933 | Hull . |
| 2,816,514 | 12/1957 | Freese . |
| 3,263,105 | 7/1966 | Heyek . |
| 3,308,361 | 7/1967 | Nakai et al. . |
| 3,633,217 | 1/1972 | Lance . |
| 3,963,380 | 6/1976 | Thomas et al. . |
| 4,167,046 | 9/1979 | Portner et al. . |
| 4,384,829 | 5/1983 | Conley et al. ........................ 417/412 |

OTHER PUBLICATIONS

Bindels, J. and Grigsby, Jr., "Considerations and Calculations about the Optimum Solenoid to be used for an Intrathoracic Artificial Heart", Trans. Amer. Soc. Artif. Int. Organs, 7:369, 1961.
Bindels, J., "Theoretical Limits of Efficiency for Solenoids to Drive Artificial Hearts", Trans. Amer. Soc. Artif. Int. Organs", 8:140, 1962.
Freebairn, D. and Hoggs, T., "Solenoid Design for a Prosthetic Heart", Trans. Amer. Soc. Artif. Int. Organs, 10:166, 1964.
Fuller, J. W., Bourland, H. M., O'Bannon, W., Liotta, D., Hall, C. W., and Bahler, A. S., "A Solenoid Powered Ventricular Bypass Pump", Trans. Amer. Soc. Artif. Int. Organs, 14:352, 1968.
Fuller, J. W., and Armijo, L., "Design Analysis for a Solenoid Blood Pump Actuator", IEEE Trans. Biomed. Eng., 16:184, 1969.
Portner, P. M., Jassawalla, J. S., and LaForge, D. H., "An Implantable Controlled Solenoid Energy System for Driving an Artificial Heart", 7th Intersoc. Energy Conv. Eng. Conf. Proc., (1972), pp. 784-791.
Jassawalla, J. S., LaForge, D. H., and Portner, P. M., "An Implantable Left Ventricular Assist System Utilizing a Controlled Solenoid Energy Converter", 10th Intersoc. Energy Conv. Eng. Conf., (1975), p. 1466.
Jassawalla, J. S., Miller, P. J., and Portner, P. M., "Evolution of an Implantable Pulsed Solenoid Cardiac Assist System", Proc. 29th Ann. Conf. Eng. Med. Biol., (1976), p. 243.
Portner, P. M., Oyer, P. E., Jassawalla, J. S., Miller, P. J., Chen, H., LaForge, D. H., and Skytte, K. W., "An Implantable Permanent Left Ventricular Assist System for Man", Trans. Amer. Soc. Artif. Int. Organs., 24, 98, (1978).
Portner, P. M., Oyer, P. E., Miller, P. J., Jassawalla, J. S., Ream, A. K., Corbin, S. D., and Skytte, K. W., "Evolution of the Solenoid-Actuated Left Ventricular Assist System: Integration with a Pusher-Plate Pump for Intra-Abdominal Implantation in the Calf", Artif. Organs 2, 402, (1978).

(List continued on next page.)

*Primary Examiner*—Edward K. Look
*Attorney, Agent, or Firm*—Fitch, Even, Tabin & Flannery

[57] ABSTRACT

A pump is described in which a flexible enclosure defines a pump chamber whose contents are expelled by movement of a pusher plate engaged with the enclosure. The pusher plate is moved by an elongate beam spring interconnecting the pusher plate with a solenoid drive mechanism. Solenoid actuation causes flexing of the beam spring from a relatively less stressed to a relatively more stressed position, the increased stress in the spring being relieved by pusher element movement. A preferred embodiment of the invention includes a symmetrical arrangement of opposed pusher elements and associated beam springs.

7 Claims, 6 Drawing Figures

OTHER PUBLICATIONS

Portner, P. M., Oyer, P. E., Jassawalla, J. S., Miller, P. J., Skytte, K. W., LaForge, D. H., Ream, A. K., Corbin, S. D., and Billingham, M. E., "Development and In Vivo Evaluation of the Solenoid Actuated Left Ventricular Assist System", Proc. Ann. Contractors Meeting, Devices & Technology Branch, NHLBI, (1978), pp. 73–74.

Portner, P. M., Oyer, P. E., Jassawalla, J. S., Miller, P. J., Skytte, K. W., LaForge, D. H., Petrek, J. S., Lee, J., Ream, A. K., and Billingham, M. E., "Development In Vivo Evaluation of Solenoid Actuated Left Ventricular As System", Proc. Annual Contractors Meeting, Device and Technology Branch, NHLBI, (1979), pp. 41–42.

PUMP AND ACTUATOR MECHANISM

This application is a continuation-in-part of U.S. patent application for Pump and Actuator Mechanism, Ser. No. 211,210, filed Nov. 28, 1980 now U.S. Pat. No. 4,384,829.

This invention relates generally to pumps and the like. More particularly, the invention relates to an improved actuator mechanism for a pump, the pump and actuator mechanism being particularly suited for use as an internally implanted blood pump.

In some instances, it may be advantageous to employ in a pump, a pair of opposed pusher elements moveable reciprocally from a relatively more displaced first position to a relatively less displaced second position for expelling the contents of the pump chamber. By way of example, a pump of this general type is shown and described in U.S. Pat. No. 4,167,046. This pump is for internal use in humans and animals as a left ventricular assist device. The device is comprised of a unitary pancake shaped deformable sac of flexible resilient blood-compatible material. A pair of oppositely acting plates on each side of the pancake shaped sac are moved toward each other to compress the sac and provide for expelling the contents of the sac. Various advantages accrue from this construction as set forth in the aforementioned patent.

In that patent, the actuator mechanism described includes a pair of arms which are pivotally mounted at one end and which are coupled by suitable linkages to the pusher plates. It is suggested in the patent that these arms be moved by a solenoid actuator such as is available from Novacor Medical Corporation, Berkeley, Calif. under the designation MK19 and MK20.

Actuators of the foregoing type generally include a solenoid which is energized from a storage capacitor in accordance with an internally stored program in a microprocessor. Energization of the solenoid results in the storage of energy in a coil spring or torsion bar. The energy stored in the spring or torsion bar is then transferred through a suitable linkage to the arms which, in turn, displace the pusher plates.

The present invention relates to improvements in the actuator design which represent a technological breakthrough in that very significant savings result in overall size and weight and in the number of required elements. This makes the device much more suitable for implantation, and increases its reliability. Moreover, although described herein in connection with a left ventricular assist device or similar pump, the invention has broader application where its particular operational characteristics are suited to move one element or opposed elements against a resisting force.

More particularly, a general object of the invention is to provide an improved actuator mechanism for moving a pusher element against a resisting force from an initial position to an end-of-stroke second position.

Another object of the invention is to provide a pump of the type in which a flexible enclosure defines a pump chamber whose contents are expelled by movement of opposed pusher elements, wherein the pump is provided with an improved actuator mechanism.

A still further object of the invention is to provide an actuator mechanism for moving opposed elements against a resisting force wherein the mechanism is compact, lightweight, and of a simpler construction than other known mechanisms of this type.

Other objects of the invention will become apparent to those skilled in the art from the following description taken in connection with the accompanying drawings wherein.

Very generally, the improved actuator mechanism includes an elongated beam spring which interconnects a pump pusher plate with a solenoid pump drive mechanism. Solenoid actuation causes flexing of the beam spring from a relatively less stressed to a relatively more stressed position, with the increased stress in the spring being relieved by pusher element movement.

A preferred embodiment of the invention is constructed for driving a pump of the type having a pair of opposed pusher plates acting on opposite sides of a disc-shaped sac to expel fluid therefrom. Opposed beam springs are each pivotally connected at one end to the associated pusher plates, and attached at the other spring end on an armature assembly pivotally connected to a frame. Each assembly includes a preload stop which holds the associated spring in the relatively less stressed position. Coordinated movement of the two assemblies toward one another, by solenoid actuation, moves the two springs toward their relatively more stressed positions, with stress relief in the beams acting to move the two pusher plates symetrically toward one another.

FIGS. 1-5 illustrate an actuator mechanism constructed according to the invention, shown for use in conjunction with a pump of the type described in the aforementioned U.S. Pat. No. 4,167,046. The pump, which is for the purpose of serving as a left ventricular assist device to be implanted in a human or animal patient, includes an enclosure 11 defining a pumping chamber 13. Opposed pusher plates 15, 17 are disposed on opposite sides of the enclosure 11 and in contact therewith. Movement of the plates toward one another acts to compress the flexible enclosure and force the contents of the chamber out through a suitable outlet duct, not shown. Greater detail of this pump chamber configuration is given in the aforementioned U.S. patent. An annular support 19 surrounds the flexible enclosure 11 to position it with respect to the remaining portions of the pump, including the actuator mechanism.

Figure 1:
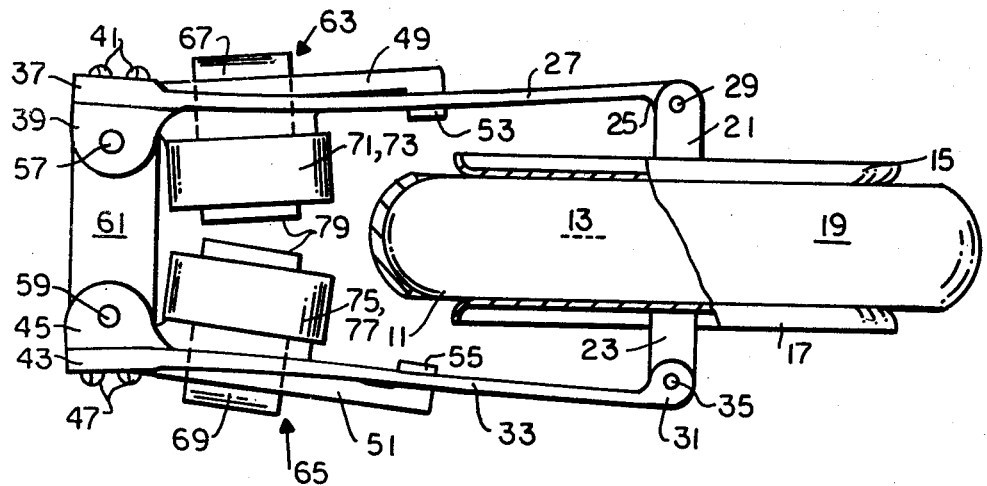
FIG. 1 is a cross-sectional schematic view of a pump constructed in accordance with the invention.
Figure 2:
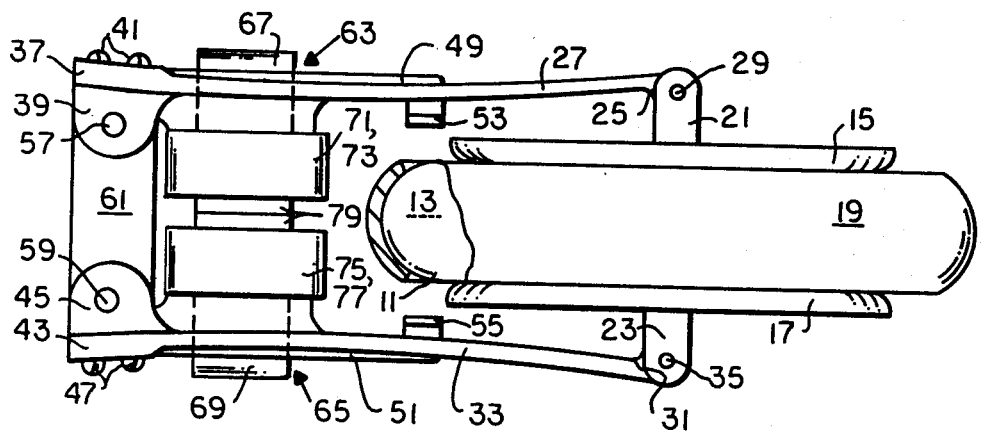
FIG. 2 is a cross-sectional schematic view similar to FIG. 1 illustrating a second condition of the pump.
Figure 3:
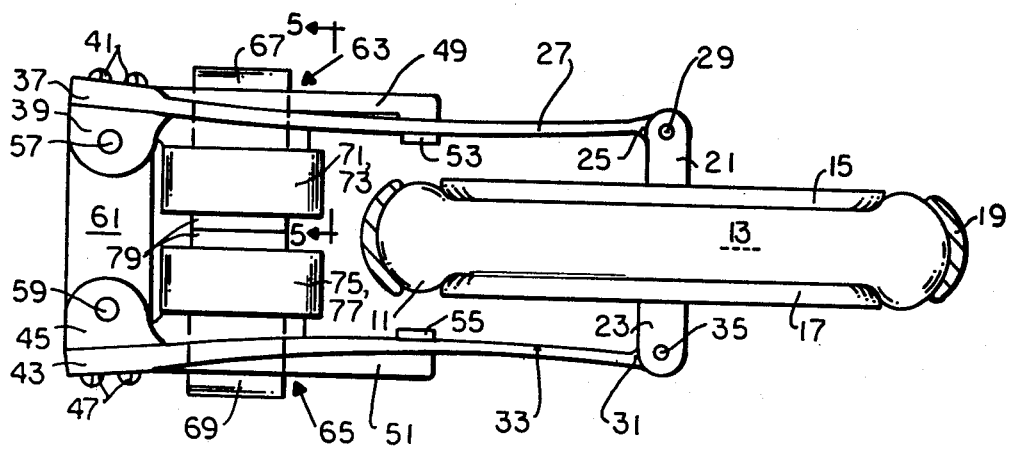
FIG. 3 is a cross-sectional schematic view of the pump of FIG. 1 illustrating a third condition of the pump.
Figure 4:
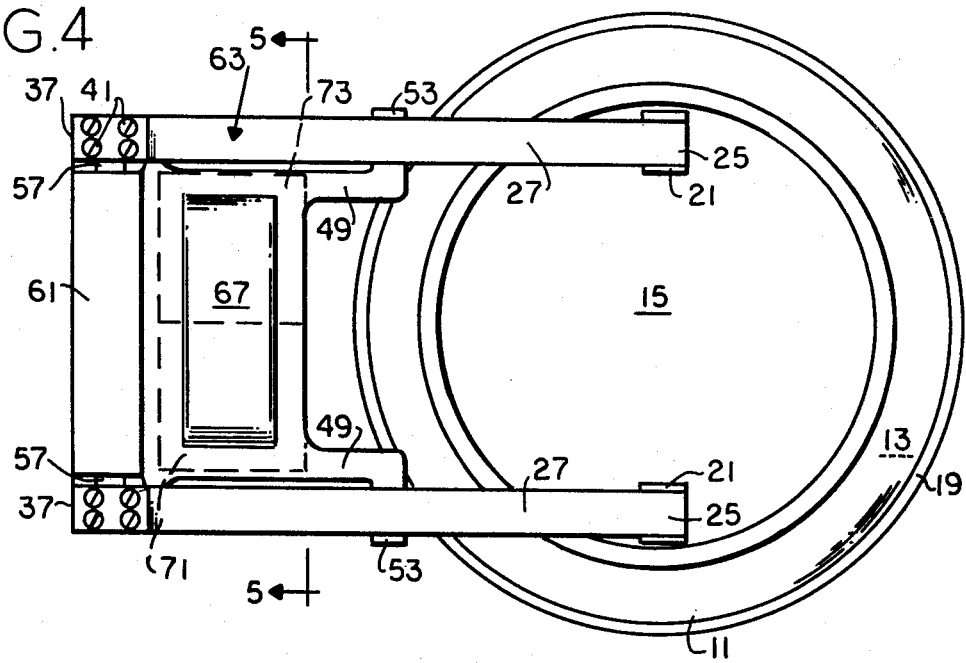
FIG. 4 is a top view of the pump of FIGS. 1-3.
Figure 5:
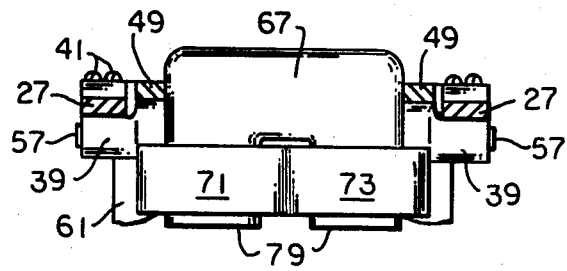
FIG. 5 is a sectional view taken on the lines 5—5 of FIGS. 3 and 4.

In the illustrated embodiment of the invention, two pairs of opposed beam springs 27, 33 are used, as shown by comparing FIGS. 1-3 with FIG. 4. However, one pair of opposed beam springs will suffice in some applications and the four springs are used in the illustrated embodiment so the solenoid means may be of minimal size. Opposed pairs of posts 21 and 23, extend from plates 15, 17 respectively, at the positions seen in FIG. 4. Posts 21 are pivotally connected to the enlarged ends 25 of a pair of beam springs 27 by pins 29. Similarly, posts 23 are pivotally connected to the enlarged ends 31 of a pair of beam springs 33 by pivot pins 35.

The ends of beam springs 27 opposite ends 25 are provided with portions 37 of slightly enlarged cross-section. The sections 37 are bolted to a support 39 by bolts 41 passing through the portions 37 into the support 39. Similarly, the ends of the beams 33 opposite the ends 31 are provided with enlarged thickness portions 43 which are bolted to a support 45 by means of bolts 47.

Each of the supports 39 and 45, respectively, is provided with a pair of arms 49 and 51, respectively, extending therefrom coextensively with the corresponding beam springs 27 and 33. Projections or preload stops 53 are provided on the free ends of the arms 49 projecting under the corresponding one of the beam springs 27. Similar preload stops 55 are provided on the free ends of the arms 51 projecting over the corresponding one of the beam springs 33. For reasons which will be explained subsequently, the mating surfaces of the portions 37 of the beam springs 27 and the support 39 lie in a plane such that the engaging points of the preload stops 53 project beyond that plane and, accordingly, preload the beam springs 27 in bending stress. A similar relationship with the preload stops 55 and the mating surfaces of the support 45 and the portions 43 of the beam springs 33 provides a preload for the beam springs 33. The result is that each of the beam springs 27 and 33 are always stressed in bending by a minimum amount provided by the preload of the preload stops 53 and 55.

Each of the supports 39 and 45 is mounted for pivotal movement about an axis through a pivot pin 57 and 59, respectively. Thus, as the support 39 pivots on the pin 57, so likewise do the sections 37 of the beam springs 27 move pivotally about the axis. Similarly, as the support 45 pivots on the axis of the pin 59, so likewise the ends 43 of the beam springs 33 pivot about the axis of the pin 59 with the support 45. Each of the pins 57 and 59 is supported in a frame 61 which comprises a portion of the general frame (not shown) of the pump which includes the enclosure support 19.

For the purpose of pivoting the beam springs about the axes of the pins 57 and 59, solenoid means are provided. The solenoid means include a pair of solenoid armatures 63 and 65 mounted, respectively, on supports 39, 45. Supports 39, 45 and attached armatures 63, 65, respectively, each forms what is referred to herein as an armature assembly. Solenoid armature 63 includes a C-shaped core 67, the free ends of which extend through mating openings in the support 39. Similarly, the solenoid armature 65 includes a C-shaped core 69, the free ends of which extend through mating openings in the support 45. The open side of core 67 faces the open side of core 69 and the free ends 79 are aligned. Each leg of the C-shaped core 67 is wound with by a coil 71 and 73. Similarly, each leg of the C-shaped core 69 is wound with by a coil 75 and 77, respectively. Energization of the coils 71, 73, 75, and 77, by suitable control means, not shown, causes the ends of the solenoid cores to be attracted toward each other.

The operation of the actuator mechanism and pump may be observed sequentially in FIGS. 1-3. FIG. 1 illustrates the apparatus in a condition in which the pump chamber 13 is full and the solenoid armatures 63 and 65 are unenergized. In this condition, the arms 49 and 51 are swung open to their widest condition as are the beam springs 27 and 33. In this condition, a preload bias is provided to the springs by the preload stops 53 and 55.

The ejection stroke is begun when the storage capacitor, not shown, energizes the solenoid coils 71, 73, 75, and 77. When energized, the armature 63 and 65 are drawn toward each other, moving the arms 49 and 51 to the position shown in FIG. 2. In this position, the inertia of the filled pump chamber 13 and compressible sac 11 retain the ends 25 and 31 of the beam springs 27 and 23 essentially in the same position as in FIG. 1. The preload stops 53 and 55 are moved away from the springs, with pivoting of supports 39, 45 causing the springs to be stressed to a more loaded condition in which they contain greater stored energy.

After closure to the position of FIG. 2, the solenoid means are held there by a relatively small latching current. If additional holding force is needed, a small permanent magnet may be used. The force of the latter may be overcome when necessary by a small reverse current in the solenoid coils.

From the condition if FIG. 2, the natural tendency for the beam springs 27 and 33 to relieve the stressed condition results in the plates 15 and 17 being moved toward each other, thus expelling the contents in the pump chamber 13. At the end of the pump stroke, shown in FIG. 3, the beam springs have returned to their less stressed condition abutting the preload stops 53 and 55. Once this has occurred, the solenoid coils are de-energized or unlatched.

Figure 6:
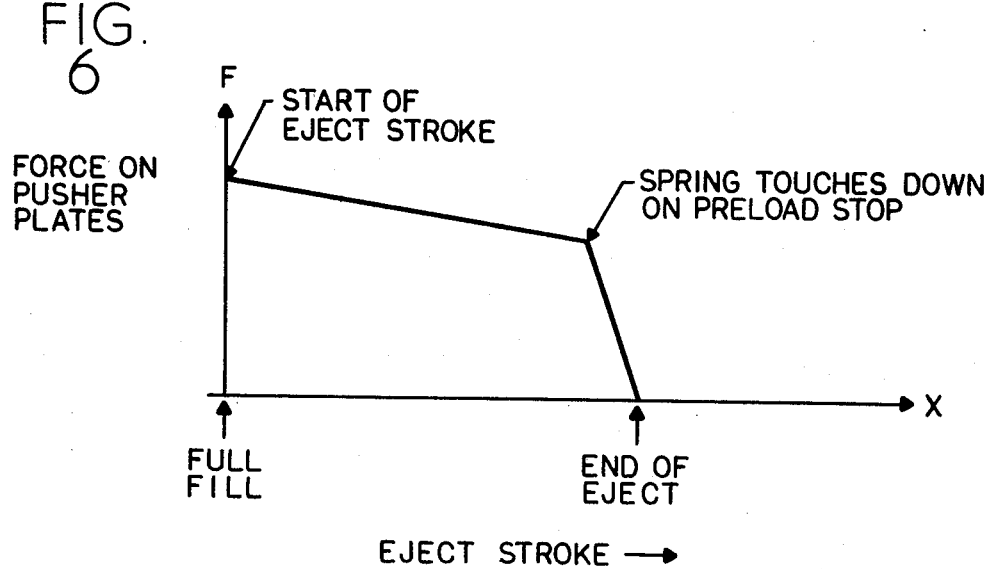
FIG. 6 is a graph illustrating the force exerted on the pusher plates by one of the beam springs with respect to the ejection stroke.

The apparatus is returned to the condition shown in FIG. 1 as the result of the cardiac systole. The solenoid gap thus increases as the supports 39 and 45 pivot about the pivot pins 57 and 59, respectively, as the plates 15 and 17 push out the ends 25 and 31 of the springs 27 and 33. A suitable detector, not shown, is provided to determine the time at which the rate of pump fill drops below a preselected threshold. At this point, a microprocessor, not shown, is programmed to resume the ventricular assist pumping function. Referring now to FIG. 6, the characteristics of the device may be observed in connection with the relationship between the force on the pusher plates 15 and 17 versus the ejection or expelling stroke distance. The nearly horizontal portion of the curve is the normal characteristic of stress relief in the beam spring. A spring with a relatively low spring constant is selected so that this portion of the curve is as horizontal as possible. It may be seen that at the furthest left-hand edge of the plot, the ejection stroke begins after filling. Ejection proceeds until the springs engage the preload stops, at which time the ejection stroke terminates as shown. The energy retained in the spring by the preloading thus is to the right of the termination of the curve in FIG. 6.

According to one aspect of the invention, the shape of the force curve in FIG. 6 to the right of the point of contact between the beam spring and the preload stop can be selected according to the construction of the preload arm. To illustrate, it can be appreciated that where a preload arm is constructed to contact an associated beam spring at the position shown in FIGS. 1-3, the slope of the force curve following such contact will reflect relaxation in the beam spring distal to the preload stop. On the other hand, the preload stop may be positioned close to the distal end of the associated beam spring, resulting in a more abrupt decline in the force curve. Further, the shape of the force curve can be varied according to the resiliency of the preload arms. With a rigid preload arm, the force curve decline may be quite abrupt, whereas a resilient spring-type preload arm can produce a more gradual drop in the force curve, evidencing the gradual loss in beam spring force as it is resisted by an increasing opposing force exerted by the preload arm. Thus a desired shape of the force curve after contact between the beam spring and the preload stop can be achieved by proper selection of the spring constants in the beam spring and preload arm and by suitable positioning of the preload stops with respect to the beam springs.

The construction and operation of the invention has been described above with reference to an actuator mechanism having one or more pairs of opposed beam springs which are under the control of a pair of coordinately movable armature assemblies. The invention also contemplates an actuator mechanism adapted for driving an asymetric deformable pump sac in which the pumping action is achieved by recurrently moving a single pusher plate attached to a deformable sac surface. The actuator includes, in addition to the pusher plate, an armature assembly which is mounted on a fixed frame for pivoting substantially in the direction of movement of the pusher plate. The nondeformed portions of the pump sac may also be supported in a fixed position with respect to the frame. One or more spring beams in the actuator mechanism is connected at one end to the pivotable armature and connected at its other end to the pusher plate. The spring is held in a relatively less stressed position at the beginning of each pumping cycle, by a rigid or spring-type preload stop. Movement of the armature from an open to a closed position, with the pusher plate in an initial deflection position, causes bending in the beam spring to a relatively more stressed position which is relieved by movement of the pusher plate in a direction which causes fluid in the pump sac to be expelled, similar to what has been described above with respect to the symetrical, two-sided pump actuator shown in FIGS. 1-3.

The invention provides a number of significant advantages. Mechanical simplicity is achieved because each preloaded spring delivers the desired output force profile without the need for motion amplification linkage. Thus, the system has few moving parts, few bearings, and is more compact, more efficient and more reliable than prior art designs. Since each beam spring acts directly on the associated pump pusher plate, no output arms are required, again producing a simpler, lighter system.

Because of the low spring constant used to produce a relatively flat output force profile (FIG. 6), peak spring force in the preloaded spring is much lower than with a linear (non-preloaded) spring, storing an equal amount of energy. As a result, peak loads on the spring, frame and bearings are half that of prior art designs, yielding a reduction in size and mass of most components, and an increase in bearing life and reliability. Moreover, the beam spring has an inherently simple geometry. It has predictable spring characteristics, can be designed with minimal stress concentration factors, and is easy to fabricate. Its simple shape allows a bolted, rather than welded, assembly, facilitating system development and optimization. In addition, because the beam spring is loaded in bending (as opposed to helical compression springs and torsion bars, where the material is loaded in shear), the endurance strength of the spring material is higher, and the spring is less sensitive to surface finish than in prior art designs. Finally, the preloaded spring design results in reduced stress amplitude at the area of highest stress level. This allows a conservative spring design with a high safety factor. Due to the spring force profile, solenoid closure may be relatively slow. This permits the implementation of a real-time energy servo. Solenoid energy can be adjusted during the final stages of closure, assuring perfect energy matching every beat. This results in quiet operation and optimum efficiency. Further to this end, the preload stop may be constructed and arranged to produce a desired force versus movement behavior in the pusher plate, as the plate approaches its end-of-stroke position.

It may be seen, therefore, that the invention provides an improved pump system and actuator therefor which are of minimal size and weight, use few parts, and are highly reliable. Various modifications of the invention in addition to those shown and described herein will become apparent to those skilled in the art from the foregoing description and accompanying drawings. Such modifications are intended to fall within the scope of the appended claims.

What is claimed is:

1. A pump comprising a flexible enclosure defining a pump chamber, a pusher element engaged with said enclosure and being movable reciprocally from a first to a second position for expelling the contents of the pump chamber, and an actuator mechanism for moving said pusher element between its said positions, said mechanism comprising an elongated beam spring having one end coupled to said pusher element, means supporting the other end of said beam spring for pivotal movement about an axis extending transversely of the beam spring axis, said supporting means including means for preloading said beam spring in one position, in which, with said pusher element in said first position, said beam spring is relatively less stressed, and means for pivoting said beam spring about said axis from said one position to another position in which, with said pusher element in said first position, said beam spring is relatively more stressed, whereby in relieving said stress, said one end of said beam spring is displaced to move said pusher element to its second position.

2. The pump of claim 1, wherein said means for preloading said beam spring includes a preload spring which is constructed and arranged to produce a desired force curve which characterizes the force of the pusher element acting against the enclosure as the pusher element approaches its second position.

3. A pump comprising a flexible enclosure defining a pump chamber, a pair of opposed pusher elements engaged with said enclosure and being movable reciprocally from a relatively more displaced first position to a relatively less displaced second position for expelling the contents of the pump chamber, an actuator mechanism for moving said pusher elements, said actuator mechanism comprising at least one pair of elongated beam springs, each having one end coupled to a respective one of said pusher elements, means supporting the ends of said beam springs opposite said one ends for pivotal movement about axes extending transversely of the major dimension of said beam spring, said supporting means including means for preloading each of said beam springs in a first position wherein, with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position, where said means for preloading each of said beam springs includes, for each spring beam, a preload spring which is constructed and arranged to produce a desired force curve which characterizes the force of the associated pusher element acting against the enclosure as the element approaches its second position.

4. In a pump having a pair of opposed pusher elements movable reciprocally from a relatively more displaced first position to a relatively less displaced second position for expelling the contents of a pump chamber, an actuator mechanism for moving said pusher elements, comprising, at least one pair of elongated beams springs, each having one end coupled to a respective one of said pusher elements, means supporting the ends of said beam springs opposite said one ends for pivotal movement about axes extending transversely of the major dimension of said beam springs, said supporting means including means for preloading each of said beam springs in a first position wherein, with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position, where said means for preloading said beam spring includes, for each beam spring, a preload spring which is constructed and arranged to produce a desired force curve which characterizes the force of the associated pusher element acting against the enclosure as that pusher element approaches its second position.

5. An actuator mechanism for moving opposed pusher elements against a resisting force from a relatively more displaced first position to a relatively less displaced second position, comprising, at least one pair of elongated beam springs, each having one end coupled to a respective one of said pusher elements, means supporting the ends of said beam springs opposite said one ends for pivotal movement about axes extending transversely of the major dimension of said beam springs, said supporting means including means for preloading each of said beam springs in a first position wherein, with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position, where said means for preloading said beam spring includes a preload spring which is constructed and arranged to produce a desired force curve which characterizes the force of the associated pusher element acting against the enclosure as the element approaches its second position.

6. An actuator mechanism for moving a pusher element against a resisting force from a relatively more displaced first position to a relatively less displaced second position, said mechanism comprising an elongated beam spring having one end coupled to said pusher element, means supporting the other end of said beam spring for pivotal movement about an axis extending transversely of the beam spring axis, said supporting means including means for preloading said beam spring in one position, in which, with said pusher element in said first position, said beam spring is relatively less stressed, and means for pivoting said beam spring about said axis from said one position to another position in which, with said pusher element in said first position, said beam spring is relatively more stressed, whereby in relieving said stress, said one end of said beam spring is displaced to move said pusher element to its second position.

7. The mechanism of claim 6, wherein said means for preloading said beam spring includes a preload spring which is constructed and arranged to produce a desired force curve which characterizes the force of the pusher element acting against the enclosure as the pusher element approaches its second position.

* * * * *

UNITED STATES PATENT AND TRADEMARK OFFICE
CERTIFICATE OF CORRECTION

PATENT NO. : 4,457,673
DATED : July 3, 1984
INVENTOR(S) : Conley, et al.

It is certified that error appears in the above-indentified patent and that said Letters Patent is hereby corrected as shown below:

Column 1, after line 7, insert the following information:

--The government has a non-exclusive, non-transferrable, irrevocable, paid-up license to practice or have practiced for or on behalf of the United States, the subject invention--.

Signed and Sealed this

Fifteenth Day of November, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 4,457,673
DATED : July 3, 1984
INVENTOR(S) : Conley, et. al.

It is certified that error appears in the above-indentified patent and that said Letters Patent is hereby corrected as shown below:

Column 1, after Title, insert --This invention was made under No 1-HV-02908 awarded by Public Health Service/National Institutes of Health; National Heart, Lung and Blood Institute. The government has certain rights--.

Signed and Sealed this

Twentieth Day of June, 1995

Attest:

BRUCE LEHMAN

Attesting Officer

Commissioner of Patents and Trademarks